United States Patent
Wang et al.

(10) Patent No.: US 11,712,354 B2
(45) Date of Patent: Aug. 1, 2023

(54) HIGHLY FLEXIBLE STENT

(71) Applicant: Hangzhou Endonom Medtech Co., Ltd, Zhejiang (CN)

(72) Inventors: Yongsheng Wang, Zhejiang (CN); Anwei Li, Zhejiang (CN); Bin Li, Zhejiang (CN)

(73) Assignee: HANGZHOU ENDONOM MEDTECH CO., LTD, Zhejiang (CN)

( * ) Notice: Subject to any disclaimer, the term of this patent is extended or adjusted under 35 U.S.C. 154(b) by 126 days.

(21) Appl. No.: 17/165,264

(22) Filed: Feb. 2, 2021

(65) Prior Publication Data

US 2021/0154034 A1    May 27, 2021

Related U.S. Application Data

(63) Continuation of application No. PCT/CN2019/098375, filed on Jul. 30, 2019.

(30) Foreign Application Priority Data

Aug. 2, 2018  (CN) .......................... 201810873465.6
Aug. 2, 2018  (CN) .......................... 201821240872.5

(51) Int. Cl.
*A61F 2/915*    (2013.01)

(52) U.S. Cl.
CPC .... *A61F 2/915* (2013.01); *A61F 2002/91575* (2013.01); *A61F 2210/0014* (2013.01)

(58) Field of Classification Search
CPC ... A61F 2/90; A61F 2/915; A61F 2002/91575
See application file for complete search history.

(56) References Cited

U.S. PATENT DOCUMENTS

| | | | |
|---|---|---|---|
| 2002/0099436 A1* | 7/2002 | Thornton | A61F 2/06 623/1.14 |
| 2004/0176832 A1 | 9/2004 | Hartley et al. | |
| 2012/0035705 A1* | 2/2012 | Giasolli | A61F 2/89 623/1.11 |

FOREIGN PATENT DOCUMENTS

CN          105769383 A   *  7/2016  ........... A61F 2/0077

OTHER PUBLICATIONS

International Search Report and Written Opinion of PCT/CN2019/098375 dated Oct. 23, 2019, 8 pages (English and Chinese).

* cited by examiner

*Primary Examiner* — Dinah Baria
(74) *Attorney, Agent, or Firm* — Rankin, Hill & Clark LLP (57) ABSTRACT

The present disclosure discloses a highly flexible stent which includes a plurality of annular supports arranged in an axial direction. The annular support is formed by a plurality of wave-shaped support units which are connected end to end. The support unit comprises a peak, a valley and a bar connected between the peak and the valley. In two adjacent annular supports, the peaks and the valleys of the support units of different annular supports are connected by first flexible connecting members. The first flexible connecting member further extends to and is wound onto at least one support unit to form a second flexible connecting member. The present disclosure provides a highly flexible stent having good compressibility, delivery compliance, and uniformity of expansion.

20 Claims, 10 Drawing Sheets

HIGHLY FLEXIBLE STENT

TECHNICAL FIELD

The present disclosure relates to the technical field of medical devices, in particular to a stent, and more particularly relates to a highly flexible stent which can be used for endovascular interventional therapy.

BACKGROUND

Peripheral vascular diseases are common manifestations of systemic atherosclerosis, the incidence of which has increased significantly in recent years, such as arteriosclerosis obliterans, arteriovenous thrombosis, aneurysms and so on, which may induce systemic atherosclerosis and cardiovascular morbidity and mortality. In the invent of a lesion formed in the peripheral blood vessel, the blood vessel becomes narrowing, and the blood flow directed to the lower limbs reduces, resulting in lack of blood supply of the lower limbs and thus necrosis of the lower limbs.

Main treatment methods include medical treatments and surgical treatments, wherein the medical treatments such as lowering blood pressure, lowering blood fat, preventing platelet aggregation and the like may delay the progression of the arteriosclerosis obliteration of the lower limbs, but cannot fundamentally eliminate vascular stenosis, occlusion and other organic lesions. Surgical treatments are classified into open surgery and endovascular interventional therapy. Endovascular interventional therapy has the advantages of minimal invasiveness, simple operation, definite curative effect and repeatable operation, which is the development direction of diagnosis and treatment of vascular diseases.

Aortic aneurysm refers to the abnormal local or diffuse expansion of the aortic wall, resulting in compression of the surrounding organs to cause symptoms, and the main risk of which is aneurysm rupture. It often occurs in ascending aorta, aortic arch, descending aorta, thoracoabdominal aorta and abdominal aorta. Aortic aneurysms can be classified into true aortic aneurysm, pseudoaneurysm and dissecting aortic aneurysm according to the structures. Aortic aneurysm causes increased pressure in the inner side of the vessel, so it expands progressively. If it has been developed for a long time, aortic aneurysm will eventually rupture, and the larger the aneurysm, the greater possibility for rupture. According to statistics, without surgical treatment, 90% patients with thoracic aortic aneurysms will die within 5 years, and ¾ patients with abdominal aortic aneurysms will die within 5 years.

The thoracic aortic endovascular repair surgery has a treatment scope covering aortic dissection, aortic penetrating ulcer, intermural hematoma of the aorta, aortic dilatation diseases such as thoracic aortic aneurysm and pseudoaneurysm, and secondary endovascular treatment for complications after aortic surgery or after TEVAR. On the other hand, EVAR has been rapidly promoted around the world since the first case of abdominal aortic endovascular repair was reported in the 1990s. Due to its advantages such as less trauma, shorter operation and hospitalization time, faster postoperative recovery, lower mortality and complication rate, EVAR has been developed rapidly in just two decades, and become the preferred treatment for abdominal aortic aneurysm.

At present, the most widely used interventional treatment devices mainly include balloon expandable stents and self-expandable stents. Regarding the self-expanding stents, closed-loop stents are commonly used, in which the peak and the valley between two axially adjacent support units of the stent are connected by a connecting bar. The closed-loop stent has the advantages that the metal coverage is large and the radial supporting force is great, so that the stent can uniformly cover the blood vessel wall and prevent plaque from falling off. However, such a design is relatively poor in flexibility, unable to adapt to the bending of complex diseased vessels. Since the vascular stent needs to be compressed, delivered and expanded during use of the stent, the stent must have good compressibility, delivery flexibility and expansion uniformity. This puts forward a very high requirement for the material and structure design of the blood vessel stents, and the existing stents cannot perfectly realize all of these performances.

SUMMARY

The technical solutions adopted by the present invention to solve the technical problem is provided as follows.

A highly flexible stent includes a plurality of annular supports arranged in an axial direction. The annular supports is formed by a plurality of wave-shaped support units connected end to end. Each of the support units includes a peak, a valley, and a bar connected between the peak and the valley. Within two adjacent annular supports, the peaks of the support units of one annular support are connected to the valleys of the support units of an other annular support by first flexible connecting members, and the first flexible connecting member further extends to and is wound onto at least one support unit to form a second flexible connecting member.

Further, in the highly flexible stent, it is preferable that the support units in different annular supports have the same wavelengths, and the supports units are respectively aligned in the axial direction and arranged in columns, and wherein within two adjacent annular supports, the first flexible connecting member is connected between a peak and a valley which are located in different columns in the axial direction.

Further, in the highly flexible stent, it is preferable that the first flexible connecting member is connected between the peak of one support unit and both the valleys of the adjacent support units of the adjacent annular support in two adjacent columns, to form a connection structure having a shape of an inverted figure eight expressed in Simplified Chinese.

Further, in the highly flexible stent, it is preferable that within one annular support, each valley is connected with the first flexible connecting member, and a portion of the peaks are connected to the first flexible connecting members.

Further, in the highly flexible stent, it is preferable that the first flexible connecting member is continuously connected with at least the second flexible connecting member in a column adjacent to the support unit to which the first flexible connecting member is connected.

Further, in the highly flexible stent, it is preferable that the first flexible connecting members connecting the support units of two axially adjacent annular supports are continuously connected to the second flexible connecting members on the support units of one of two axially adjacent annular supports.

Further, in the highly flexible stent, it is preferable that the first flexible connecting members connecting the support units of two axially adjacent annular supports and the second flexible connecting members on the support unit of one of the two axially adjacent annular supports are formed as one-piece structure.

Further, in the highly flexible stent, it is preferable that the first flexible connecting member and the second flexible connecting member of at least two adjacent columns in the axial direction are formed as one-piece structure from a proximal end to a distal end.

Further, in the highly flexible stent, it is preferable that the second flexible connecting member is spirally wound on the support unit with a space between every adjacent turns.

Further, in the highly flexible stent, it is preferable that the spirally winding is wound clockwise or counterclockwise.

Further, in the highly flexible stent, it is preferable that the support units comprise wound support units with the second flexible connecting members wound there around, and bare support units without a second flexible connecting member wound there around, and wherein the wound support units and the bare support units are alternately arranged.

Further, in the highly flexible stent, it is preferable that within a same annular support, the wound support units and the bare support units are alternately and repeatedly arranged.

Further, in the highly flexible stent, it is preferable that in the axial direction, the wound support units and the bare support units of different annular supports are alternately and repeatedly arranged in a column.

Further, in the highly flexible stent, it is preferable that the wound support unit is a full-wound support unit in which the peak, the bar and the valley are all wound by the flexible connecting member, or the wound support unit is a partial-wound support unit in which the flexible connecting member is wound around the support unit from the peak to the bar, or from the valley to the bar.

Further, in the highly flexible stent, it is preferable that the first flexible connecting member and the second flexible connecting member are respectively formed as a linear structure, a strip structure or a ribbon structure.

Further, in the highly flexible stent, it is preferable that the annular support is an unequal-height-wave support formed by high-height-wave support units and low-height-wave support units, and wherein the peaks of the low-height-wave support units are connected to the first flexible connecting members, and the peaks of the high-height-wave support units are unconnected to the first flexible connecting members.

Further, in the highly flexible stent, it is preferable that the first flexible connecting member are connected between the peak and the valley of support units in different annular supports by means of knotting or winding.

Further, in the highly flexible stent, it is preferable that the stent further comprises a tubular membrane, and the annular supports are axially arranged and fixed on an inner surface or/and an outer surface of the membrane.

Further, in the highly flexible stent, it is preferable that the annular support is an unequal-height-wave support formed by high-height-wave support units and low-height-wave support units, and the unequal-height-wave support is fixed on the out surface or the inner surface of the membrane, and wherein the low-height-wave support units are fixed to the membrane, and the peaks of the high-height-wave support units are unfixed to the membrane.

Further, in the highly flexible stent, it is preferable that the membrane comprises an inner membrane layer and an outer membrane layer, and the annular supports are arranged between the inner membrane layer and the outer membrane layer.

The present disclosure provides a stent, which has a plurality of annular supports arranged axially. The peaks and the valleys of a plurality of annular supports are connected by first flexible connecting members. The first flexible connecting member further extends to and is wound onto at least one support unit to form a second flexible connecting member. Due the connection by the first and second flexible connecting members, the stent is easy to bend after expanding with a good compliance. The whole stent has a good compressibility, delivery compliance, and uniformity of expansion.

BRIEF DESCRIPTION OF THE DRAWINGS

The present disclosure will be further described in detail below with reference to the accompanying drawings and embodiments, in which.

DESCRIPTION OF THE EMBODIMENTS

In rule to make the technical features, objective, and advantages of the present disclosure more apparent, embodiments of the present disclosure will be described in detail with reference to accompanying drawings.

In the present disclosure, the term "proximal end" refers to a portion of the stent or stent component that is adjacent to the heart of the patient in the direction of blood flow, whilst the term "distal end" refers to a portion thereof that is remote from the heart of the patient.

First Embodiment

Figure 1:
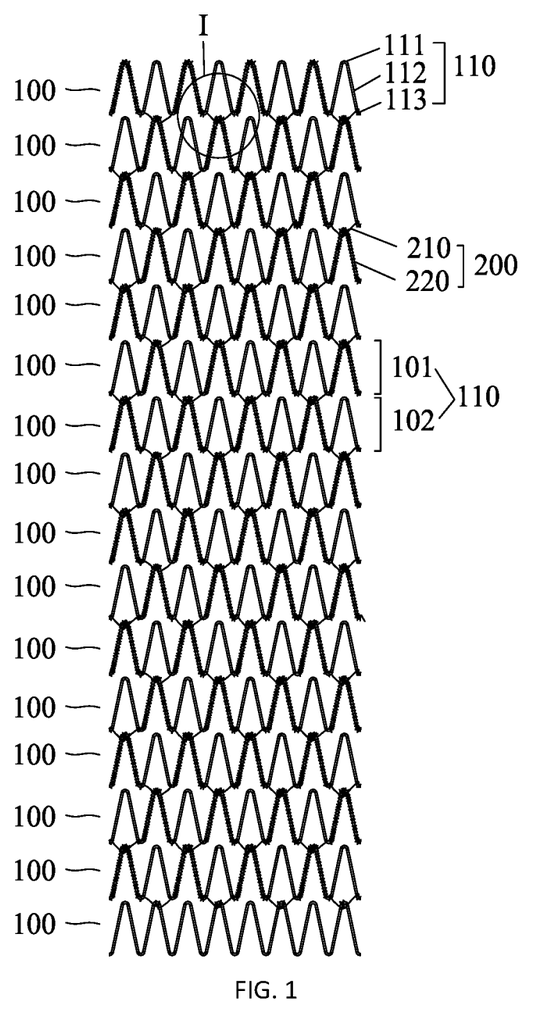
FIG. 1 is a schematic structural view of a stent according to a first embodiment of the present disclosure, in which the stent is in an expanded state.

A highly flexible stent includes a plurality of annular supports 100 arranged in an axial direction. The annular support 100 is formed by a number of wave-shaped support units 110 connected end to end. The support unit 110 includes a peak 111, a valley 113, and a bar 112 connected therebetween. Within two adjacent annular supports 100, the peaks 111 of a plurality of support units 110 in one annular support 100 are connected to the valleys 113 of a plurality of support unit 110 in the other annular support 100 by first flexible connecting members 210. The first flexible connecting member further extend to and wound around at least one of the support units 110 to form a second flexible connecting member 220.

The stent of this embodiment is a bare stent without a membrane. The stent includes a plurality of annular supports 100 arranged sequentially in parallel and spaced apart, from the proximal end to the distal end. Adjacent two annular supports 100 are connected by a plurality of first flexible connecting members 210, to thereby form a tubular stent. In the first embodiment, the number of the loops of the annular supports 100 is 16, and the number of the loops of the first flexible connecting members 210 is 15. A distance between two adjacent annular supports 100 is 0.3 to 0.5 mm.

It is preferable that the stent has a structure in which closed loops and open loops are alternately arranged. The term 'closed loops' refer to the diamond-shaped units which are formed by a portion of support units 110 of the annular support 100 connected with the peaks or valleys of the axially adjacent annular support 100 through the first flexible connecting members 210. The term 'open loops' refer to unconnected structures which are formed by a portion of support units 110 of the annular support 100 with the peaks or valleys not connected with the axially adjacent annular support 100 through the first flexible connecting member 210. The unconnected peaks or valleys are not restricted. When the stent is bending, the peaks of the open loops which are not restricted are adapted for movements according to the stent.

Figure 2:
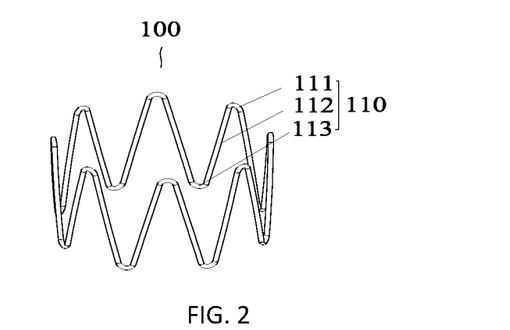
FIG. 2 is a schematic structural view of an annular support of the first embodiment of the present disclosure.

As shown in FIG. 2, the annular supports 100 form the main body of the whole blood vessel stent. Each annular support 100 has an annular configuration formed by support units 110 connected end to end. The support unit 110 includes a peak 111 and a valley 113 between which a bar 112 is provided. As far as the wave height, the annular supports 100 include equal-height annular support in which all the support units 110 have the same wave heights, or unequal-height annular support in which the support units have different wave heights. Within a same blood vessel stent, only one type of annular supports 100 may be included, alternatively two kinds of annular supports may be combined together to form the stent. In this embodiment, the annular supports 100 are equal-height. The annular supports 100 of this embodiment are equal-height annular supports which are formed by a plurality of Z-shaped or sinusoidal support units. Each of the Z-shaped or sinusoidal support units has a peak 111 and an adjacent valley 113, between which there is a bar 112. In the first embodiment, each annular support 100 is woven by using a hyperelastic nickel-titanium wire. The nickel-titanium wire has a relative small diameter which may be ranged from 0.15 mm to 0.3 mm. In this embodiment, the annular support 100 is woven by a nickel-titanium wire with a diameter of 0.2 mm. The number of the Z-shaped or sinusoidal support units 110 is 8, and the wave height of the annular support 100 is 5.5 mm.

As far as the shape of the stent, the stent of the present disclosure may be an equal-diameter stent in which the annular supports 100 have the same diameters, or an unequal-diameter stent in which the annular supports 100 have different diameters. The structure and the connecting manner of the flexible connecting member 200 in the unequal-diameter stent and the equal-diameter stent are the same. In this embodiment, the equal-diameter stent is taken as an example for detailed illustration.

With regard to the equal-diameter stent, there are two types of support units 110, one type of which is that the support units 110 in different loops in the axial direction have the same wavelength, and the support units 110 of different annular supports in the axial direction may be axially arranged correspondingly. That is, the axially adjacent peaks are aligned to each other and the axially adjacent valleys are aligned to each other. Alternatively, the support units 110 of different annular supports may be arranged to be offset from each other, that is, two axially adjacent support units are offset from each other with a distance. For example, the peak 111 of one support unit 110 is aligned with the bar 112 of the other support unit 110 in the axial direction, thus forming a spiral arrangement. In the present disclosure, it is preferred that the support units 110 in different loops in the axial direction have the same wavelengths, with the axially adjacent peaks aligned in a column and the axially adjacent valleys aligned in a column. As such, within two adjacent annular supports 100, the first flexible connecting member 210 are connected between the peak 111 and the valley 113 of two support units 110 in different columns.

The other type is that the support units 110 in different loops in the axial direction have different wavelengths. It is also possible to make the support units aligned axially. For example, a support unit of one annular support is corresponding to two or more support units 110 of another annular support. The support units 100 in different loops in the axial direction may be arranged to be offset from each other.

In the present disclosure, the flexiblity of the first flexible connecting member 210 and the second flexible connecting member 220 means that they are able to be bent and twisted freely, but are unextendable or slightly extensible in the axial direction. Preferably, the first flexible connecting member 210 and the second flexible connecting member 220 each are formed as a linear structure, a strip structure, or a ribbon structure. It is also preferable that the first flexible connecting member 210 and the second flexible connecting member 220 are formed as a linear structure, strip structure, or ribbon structure which is continuously wound between a plurality of peaks 111 and valleys 113, and on different support units 110 in the axial direction. Among the linear structure, the strip structure, and the ribbon structure, the linear structure is preferred.

The first flexible connecting members 210 are connected between the peaks 111 and the valleys 113 of the support units 110 in two adjacent loops in the axial direction. In particular, the first flexible connecting member 210 is connected between a valley 113 at the distal end of one support unit 110 and a peak 111 at the proximal end of a closest support unit 110 in an adjacent column and in an adjacent loop, by way of knotting or winding. The way of knotting means that two ends of the first flexible connecting member 210 are respectively tied to the valley 113 and the peak 111 by knots. The way of winding means that the first flexible connecting member 210 is wound around the valley 113 and the peak 111. The length of the portion of the first flexible connecting member 210 between the peak 111 and valley 113 is determined as required.

The first flexible connecting member 210 and the second flexible connecting member 220 may be separately provided, i.e., both ends of the first flexible connecting member 210 are wound or knotted on the peak 111 and the valley 113, and both ends of the second flexible connecting member 220 are wound or knotted on the support unit 110. It is also possible that the first flexible connecting member 210 and the second flexible connecting member 220 are continuously provided. Preferably, the first flexible connecting members 210 and the second flexible connecting member 220 are connected together or are formed as one-piece structure. There are two cases for the one-piece structures, one is that the first flexible connecting member 210 between a pair of peak 111 and valley 113 is integrally formed with the second flexible connecting member 220 on the same support unit 110. The other case is that the first flexible connecting members 210 and the second flexible connecting members 220 are continuously wound between a plurality of peaks 111 and valleys 113 in the axial direction, and on different support units 110. It is particularly preferable that the first flexible connecting members 210 connected between the supporting units 110 in two loops are integrally formed with the second flexible connecting members 220 which are wound around one of the two loops.

In a further embodiment, the first flexible connecting member 210 is at least continuously connected to the second flexible connecting member 210 on one of the two support units in adjacent columns of an adjacent annular support. The continuous connection means that the first flexible connecting member 210 and the second flexible connecting member 220 are formed as one-piece structure, or they are connected together by knotting or other means, such that there is a tensioning force between them. As the first flexible connecting members 210 connected between the support units 110 in two adjacent loops in the axial direction are continuously connected to the second flexible connecting members 220 wound on the support units in adjacent columns, the continuity and stability of the whole structure of the stent is further enhanced. In a further embodiment, the first flexible connecting members 210 connected between two adjacent annular supports in the axial direction and the second flexible connecting members 220 wound on one of the two adjacent annular supports are integrally formed as a linear structure, strip structure or a ribbon structure.

The first flexible connecting member 210 between a pair of peak 111 and valley 113 may be wound around or knotted to the peak 111 and valley 113 respectively. The length of the portion of the first flexible connecting member 210 between the peak 111 and the valley 113 is determined according to the bending degree requirements and the performance of the stent itself, and it is not limited in present disclosure. Preferably, the connection ensures that the support units 110 in the axial direction are aligned without twist or radially offset, and thereby maintaining the whole stent in a tubular structure.

With regard to the second flexible connecting members 220 provided on the bars 112 of the support units 110, there are a plurality of implementations depending on the winding lengths of the second flexible connecting members 220, which can be classified into full-wound support units and half-wound support units. The full-wound support unit is the case that the entire support unit 110 is wound with the second flexible connecting member 220, whilst the half-wound support unit is only partially wound by the second flexible connecting member 220. That is, it is preferable that the wound support unit 101 is a full-wound support unit in which the second flexible connecting member 220 is wound around all of the peak 111, the bar 112 and the valley 113 of one support unit 110. Alternatively, it may also be preferable that the wound support unit 101 is a half-wound support unit with the second flexible connecting member 220 wound around the support unit 110, from the peak 111 to the bar 112, or from the valley 113 to the bar 112. The second flexible connecting member 220 on the wound support unit 101 is spirally wound on the support unit 110 with several circles, and a space is defined between every adjacent circles of the second flexible connecting member. The spirally winding is winding in a clockwise direction or a counterclockwise direction.

The arrangement of the wound support units 101 has the advantage that two axially adjacent supports 100 can be connected as an integral structure by the continuous first flexible connecting members 210 and second flexible connecting members 220. In the meanwhile, some of the peaks 111 are skipped due to the winding manner, such that these peaks are not restricted on the first flexible connecting members 210, as a result, the stent generally includes bare support units 102 which are able to move freely, thereby ensuring both the stability and the compliance. Continuous winding makes sure the continuity between two adjacent annular supports 100, and thus the continuity of the whole stent, improving the radial supporting strength of the stent and the overall connection stability of the stent.

Within the first flexible connecting members 210 arranged in a loop between two annular supports 100, there are multiple arrangement implementations for the first flexible connecting members 210. For example, the first flexible connecting members 210 in a same loop are connected in the same direction, that is, the peaks 111 in one annular support 100 are connected only to the left-side-adjacent valleys 113, or connected only to the right-side-adjacent valleys 113. Alternatively, the first flexible connecting members 210 in a same loop are connected in different direction, that is, the peaks 111 in one annular support 100 can be connected with the left-side-adjacent valleys 113 or the right-side-adjacent valleys 113. It is also possible that the first flexible connecting member 210 is connected between the peak 111 of one support unit 110 and both the valleys 113 of two adjacent support units 110 in an adjacent annular support in two adjacent columns, to thereby form a connection structure having a shape of an inverted, truncated V, as shown in dotted circle 240 of FIG. 4. Such a connection can make the connection therebetween more stable and prevent twist and offset between two adjacent annular supports 100.

Since a portion of the support units 110 are wound by the second flexible connecting members 220, and thus the support units 110 include wound support units 101 which are wound by the second flexible connecting members 220 and bare support units 102 which are not wound by the second flexible connecting members 220. The wound support units 101 and the bare support units 102 are alternately and repeatedly arranged in a loop. In the axial direction, the wound support units 101 and the bare support units 102 in different loops are arranged alternately in a column. Specifically, the term 'alternately arranged' means that the wound support units 101 and the bare support units 102 are arranged alternately and repeatedly according to a certain rule. That is, in a same annular support 100, the wound support units 101 and the bare support units 102 are arranged alternately and repeatedly in a loop according to a certain arrangement rule, and the arrangement rule means the alternating rule of the wound support units 101 and the bare support units 102, which may be a combination of 1 to 4 wound support units 101 and 1 to 4 bare support units 102 that is arranged repeatedly. For example, one wound support unit 101 and one bare support unit 102 are alternated, one wound support unit 101 and two bare support units 102 are alternated, two wound support units and one bare support unit 102 are alternated etc. The arrangement rule is determined according to actually requirements on the compliance of the stent, the support strength etc, and it is not limited in the present disclosure.

In this embodiment, each of the valleys 113 is connected to a first flexible connecting member 210, and a portion of the peaks 111 are connected with the first flexible connecting members 210. Such arrangement of the first flexible connecting members 210 allows the wound support units 101 and the bare support units 102 to be alternately arranged in the same wave-shaped support 100.

The arrangement of the support units 110 in different loops also follows an alternating rule. The wound support units 101 and the bare support units 102 in different loops are arranged alternately and repeatedly in a column. Likewise, the arrangement rule may be set freely according to the compliance requirement, which may be a combination of 1 to 4 wound support units 101 and 1 to 4 bare support units in the axial direction repeatedly arranged. For example, in the axial direction, one wound support unit 101 and one bare support unit 102 are alternated, one wound support unit 101 and two bare support units 102, two wound support units 101 and one bar support unit 102 are alternated etc. In the axial direction, the non-corresponding support units 110 may also follow to the above alternating rule, and be shifted by a certain distance in the circumferential direction so as to form a spiral alternated arrangement.

Figure 3:
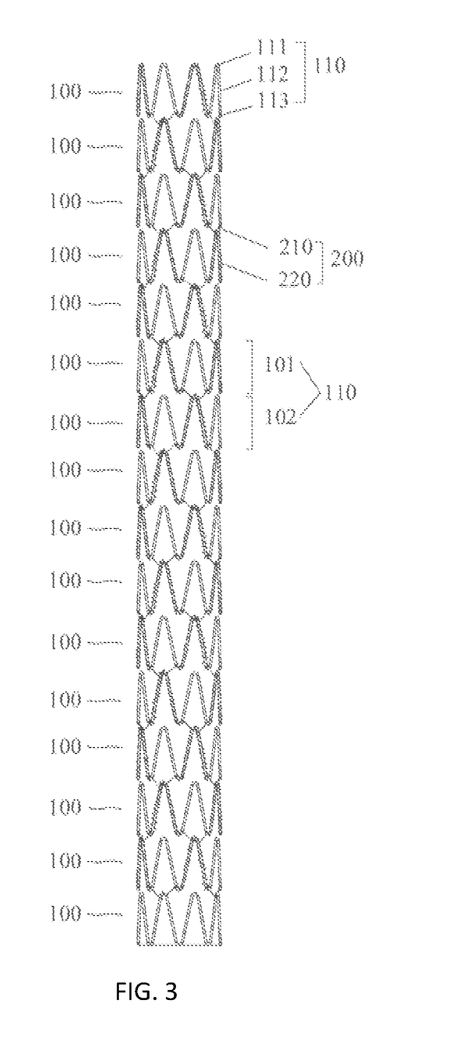
FIG. 3 is a schematic structural view of the stent according to the first embodiment of the present disclosure.

In this embodiment, as shown in FIG. 3, the annular supports 100 are axially connected by the first flexible connecting members 210 and the second flexible connecting members 220, which are formed as an one-piece structure. On the first annular support 100 at the proximal end, the second flexible connecting member 220, starting from a valley 113 of the annular support 100, is wound clockwise along the bar 112, the peak 111 to the next valley 113, and then the first flexible connecting member 210 is wound downwardly through the adjacent peak 111 of the second annular support 100, and then runs upwardly, the second flexible connecting member 220 is then wound around a valley 113 of the first annular support 100, and the winding is repeated in this way. The first flexible connecting members 210 are wound on the annular support 100 at every other peak 111. The first flexible connecting member 210 and the second flexible connecting member 220 return to a valley 113 which is located in front of the initial position on the annular support 100 after running for a loop. The second annular support 100 is wound from a rear valley 113 with respect to the winding position of the first annular support 100 in the same manner as for the first loop. The winding is repeated in above manner until the next-to-last annular support at the distal end. The first flexible connecting members 210 and the second flexible connecting members 220 are formed as an one-piece structure. The first flexible connecting members 210 and the second flexible connecting members 220 used in the present disclosure have a linear structure of polymer material or metal material, preferably PET wire, PP wire, PTFE wire, with a diameter ranged from 0.02 to 0.05 mm. In this embodiment, a PTFE wire with a diameter of 0.03 mm is used. Alternatively, a relatively thin memory alloy wire such as a nickel-titanium alloy wire, or stranded wires of relatively small diameters. The combination of the stranded wires may be a combination of wires of polymeric materials, a combination of wires of metallic materials, or a combination of wires of polymeric materials and wires of metallic materials. The annular support at the distal end is connected with the first flexible connecting members 210 at a portion of the peaks, and the support units themselves do not have second flexible connecting members 220 extending thereon, and therefore they are formed as bare support units 102.

Figure 4:
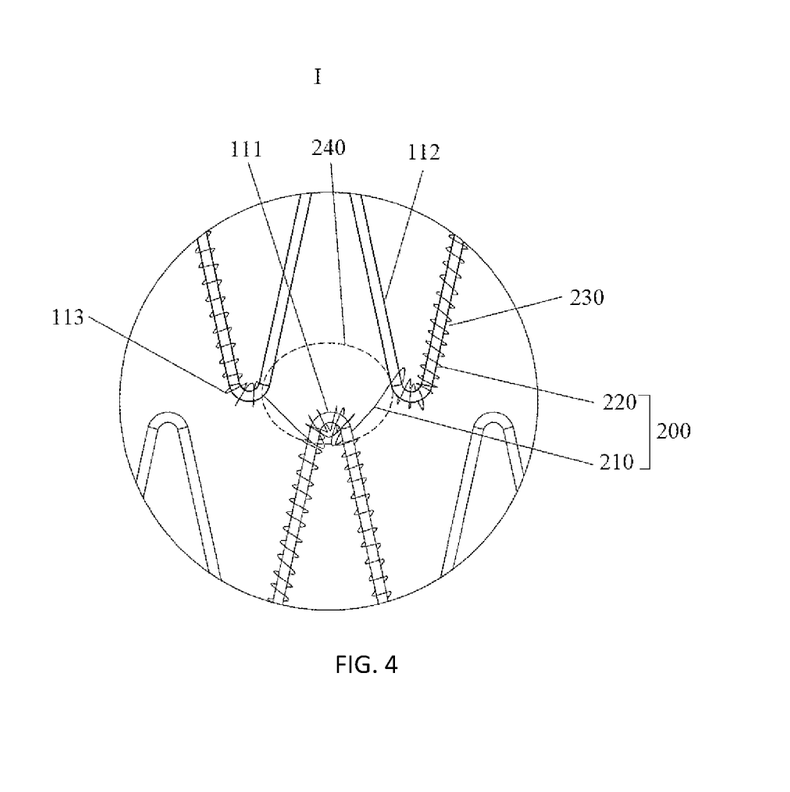
FIG. 4 is an enlarged view of a portion I of FIG. 1.

As shown in FIG. 4, in this embodiment, the first flexible connecting members 210 and the second flexible connecting members 220 are wrapped around the annular supports 100 by way of winding. The first flexible connecting member 210 starts from a valley 113 of a former annular support 100, and runs downwardly and is wound around a peak 111 of a next annular support, and then runs upwardly back to a valley 113 of the former annular support. The first flexible connecting member 210 is wound for 2 to 4 circles at the peak 111 or the valley 113. Alternatively, the first flexible connecting members 210 are knotted to and fixed at the peaks 111 and the valleys 113.

In this embodiment, the valleys 113 of axially adjacent two annular supports 100 are aligned in same axial directions, i.e. the valleys 113 of one annular support 100 are aligned to the valleys 113 of the axially adjacent annular support 100, and the peaks 111 of one annular support 100 are aligned to the peaks 111 of the axially adjacent annular support 100. The first flexible connecting members 210 are wound around and fixedly connected to adjacent annular supports 100 at every other peak 111, thereby establishing a stable diamond-shaped closed loop between the two adjacent annular supports 100. Such stable closed loop ensures the overall radial and axial stability of the stent. In addition, the stent also includes bare support units 102 which have a plurality of unrestricted peaks 111, which ensures a certain space for movement of the annular support 100 and improves the compliance of the stent. On the other hand, the adjacent annular supports 100 are connected by the first flexible connecting members 210 and the second flexible connecting members 220, which facilitate to improve the bending compliance of the stent.

Second Embodiment

This embodiment is a modification on the basis of the first embodiment.

Figure 5:
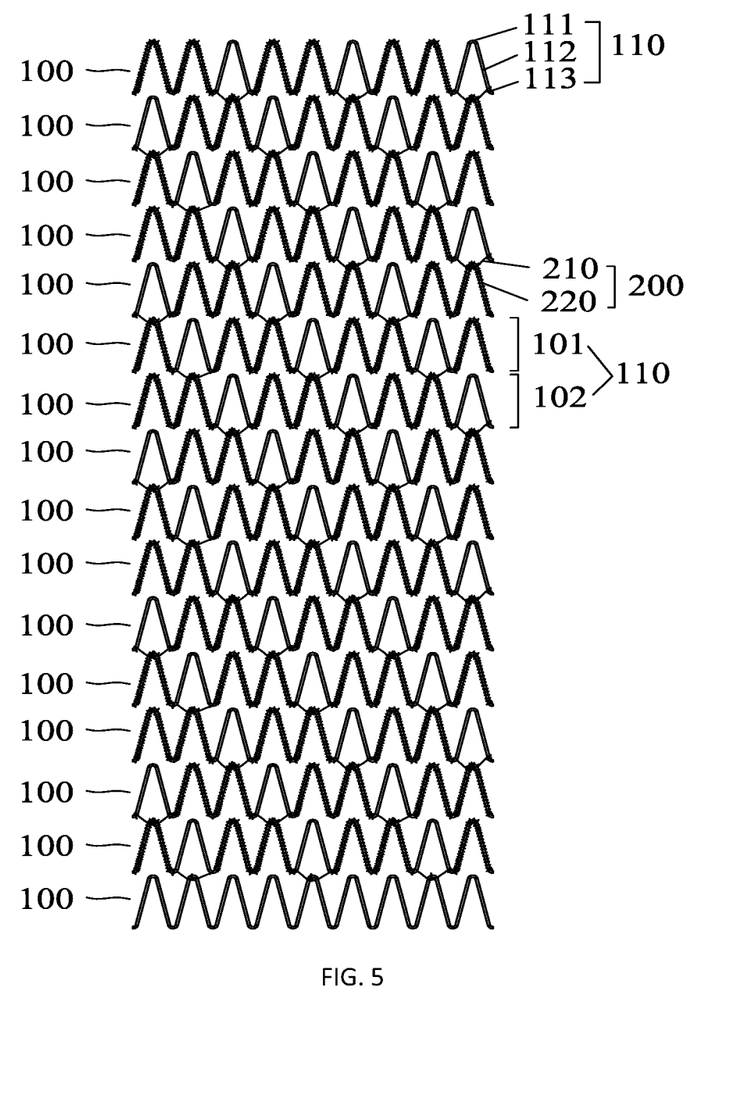
FIG. 5 is a schematic structural view of a stent according to a second embodiment of the present disclosure.

As shown in FIG. 5, the annular supports 100 according to this embodiment of the present disclosure are equal-height-wave shaped supports, and the stent is formed by connecting a plurality of annular supports 100 and multiple loops of first flexible connecting members 210 and second flexible connecting members 220. This embodiment differs from the first embodiment in that the wound support units 101 and the bare support units 102 are alternately arranged in a manner different from that of the first embodiment. In a same annular support, an alternating rule is formed that two wound support units 101 and one bare support unit are alternately arranged, for a loop. In the axial direction, an alternating rule is formed that two wound support units 101 and one bare support unit alternately arranged. The first flexible connecting members 210 and the second flexible connecting members 220 are continuously wound around two support units 110, and then leave one support unit 110 alone and continue, that is, one peak 111 is connected with two adjacent valleys 113. Adjacent wound peaks 111 are spaced apart by two peaks 111 therebetween which are not restricted by the first flexible connecting members 210, and thus the number of unrestricted peaks 111 is greater than that in the first embodiment, which further improves the compliance of the stent.

In this second embodiment, as shown in FIG. 5, the first annular support 100 at the proximal end is wound around by the second flexible connecting member 220 which starts from a valley 113 at the initial position to form a full-wound support unit, and then to a next valley 113. After two support units 110 are wound clockwise successively, the first flexible connecting member 210 is wound downwardly at the valley 113, through a peak 111 of the second annular support 100. Then the first flexible connecting member runs upwardly back to the first annular support at a valley which is spaced apart from the former wound valley by one peak, and winding is repeatedly in the clockwise direction until to the valley at the initial position, and knotted and fixed there. The second annular support is wound from a valley at a position next to what is aligned to the initial position for winding the first annular support.

Other structures are the same as those in the first embodiment, and thus will not be described here again.

Third Embodiment

This embodiment is a modification on the basis of the first embodiment.

Figure 6:
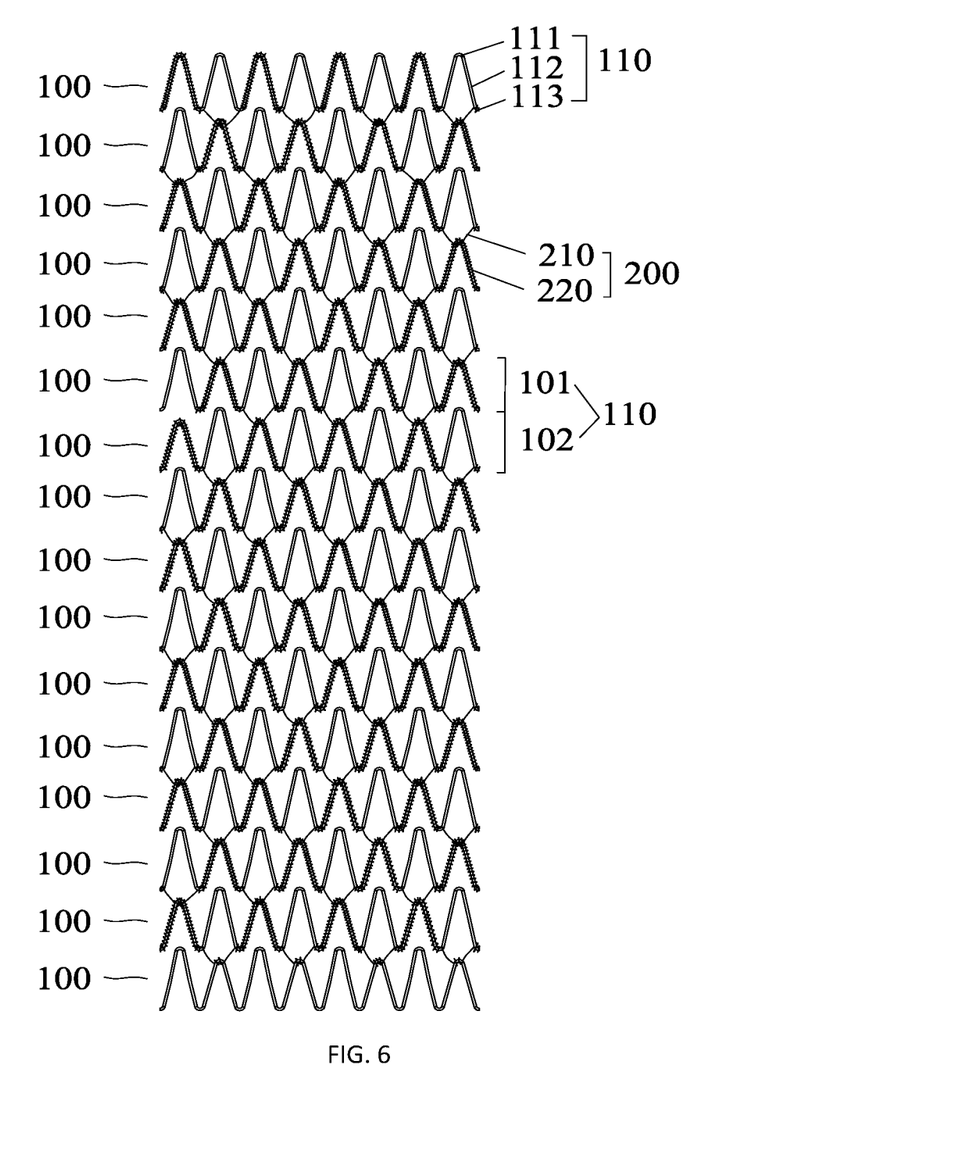
FIG. 6 is a schematic structural view of a stent according to third embodiment of the present disclosure.

As shown in FIG. 6, the third embodiment of the present disclosure differs from the first embodiment in that there are two types of annular supports 100, namely, equal-height-wave supports and unequal-height-wave supports. The first annular support at the proximal end is an equal-height-wave support, and the remaining annular supports are unequal-height-wave supports. The unequal-height-wave support is formed by one high-height-wave support unit alternately arranged with one low-height-wave support unit and repeatedly arranged. It is to be understood that in other embodiment, it is also possible that two or more high-height-wave support units are alternately arranged with one low-height-wave support unit, or one high-height-wave support unit is alternately arranged with two or more low-height-wave support units, or two or more high-height-wave support units are alternately arranged with two or more low-height-wave support units.

As shown in FIG. 6, in the third embodiment, the first annular support 100 at the proximal end is an equal-height-wave support. Form the second annular supports 100, the annular supports are unequal-height-wave supports axially arranged. In the unequal-height-wave support, the difference in height between the high-height-wave support unit and the low-height-wave support unit is ranged between 0.5 mm and 1 mm. The annular supports 100 are unequal-height-wave support formed by a plurality of high-height-wave support units and a plurality of low-height-wave support units, with the peaks 111 of the low-height-wave support units connected to the first flexible connecting members 210, and the peaks 111 of the high-height-wave support units not connected to the first flexible connecting members 210.

Specifically, the second flexible connecting member 220 is wound from a valley 113 of the first annular support 100 at the initial position, wound clockwise around a bar 112, and a peak 111. Then at a next valley 113, the first flexible connecting member 210 is wound downwardly through a peak 111 of the low-height-wave support unit 110 of the second loop of annular support 100, and runs upwardly back to and is wound around a valley 113 of the first annular support 100. The winding is continued in the clockwise direction in this manner until to the valley in front of the initial position, and knotted and fixed there. The second annular support is wound from a valley of a position next to what is aligned to the winding position of the first annular support. The winding method is the same as the first embodiment. In this embodiment, the annular supports 100 have high-height-wave support units 110 and low-height-wave support unit 110 which are alternately arranged, such that the bending degree of the annular supports 100 are increased and the flexibility of stent is improved.

Other structures are the same as those in the first embodiment, and will not be described here again.

Fourth Embodiment

This embodiment is a modification on the basis of the first embodiment.

Figure 7:
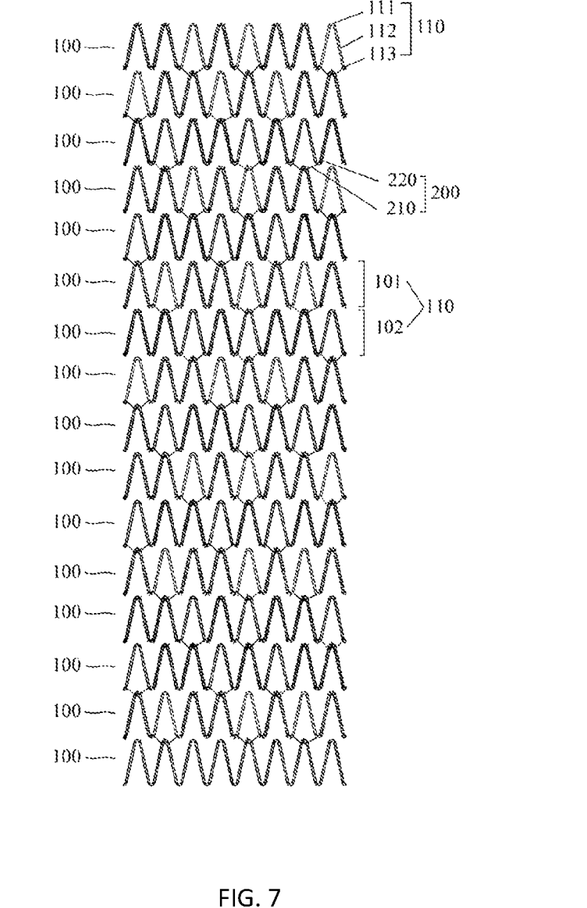
FIG. 7 is a schematic structural view of a stent according to fourth embodiment of the present disclosure.

As shown in FIG. 7, the present embodiment differs from the first embodiment in that the wound support units 101 and the bare support units 102 are alternately arranged in a manner different from that of the first embodiment. Within a same annular support, two wound support units 101 is followed by one bare support unit 102, then one wound support unit 101, and finally one bare support unit 102, and then repeated according to such an alternating rule to form a loop. In the axial direction and in the first column, except for the first one which is a wound support unit 101, an alternating rule is formed among the remaining support units such that one bare support unit 102 and two wound support units 101 are alternately arranged. In the adjacent second column, an alternating rule is formed such that two wound support units 101 and one bare support unit 102 are alternately arranged. In the third column, an alternating rule is formed such that one bare support unit 102 and two wound support units 101 are alternately arranged. The fourth column is the same as the first column. In the fifth column, except for the first one which is a bare support unit 102, the remaining support units are arranged such that a wound support unit 101 and two bare support units 102 are alternately arranged. The sixth column is the same as the first column, and the seventh column is the same as the second column. The support units are arranged in this manner. The first flexible connecting member 210 connects one peak 111 to two adjacent valleys 113, two wound peaks are spaced apart by one or two peaks 111 which are not restricted by the flexible connecting members 200. That is, within an annular support 100, each of the valleys 113 are connected to the flexible connecting members whilst only a portion of the peaks 111 is connected to the first flexible connecting members 210.

In the fourth embodiment, as shown in FIG. 7, the first annular support 100 is wound clockwise by the flexible connecting member 200 from a valley 113, after two adjacent peaks 111 have been successively wound, the flexible connecting member 200 runs downwardly at the third valley 113 and wound on a peak 111 of the second annular support 100, and then runs upwardly back to the first annular support 100 and wound around a valley thereof, and then wound clockwise around one wave of the annular support, and runs downwardly at the valley 113 to wound on the peak 111 of the second annular support, and then runs upwardly back to the valley 113 of the first annular support. In such a manner the flexible connecting member is wound clockwise back to the valley 113 of the initial position and knotted and fixed there. The second loop of annular support is wound from position of a valley 113 next to what is aligned to the winding position of the first annular support 100, with a winding method the same as that for the first annular support. In this embodiment, the unrestricted peaks 111 and valleys 113 have a number greater than that of the first embodiment, thus further improving the compliance of the stent.

Other structures are the same as those in the first embodiment, and will not be described here again.

Fifth Embodiment

This embodiment is a modification on the basis of the first embodiment.

Figure 8:
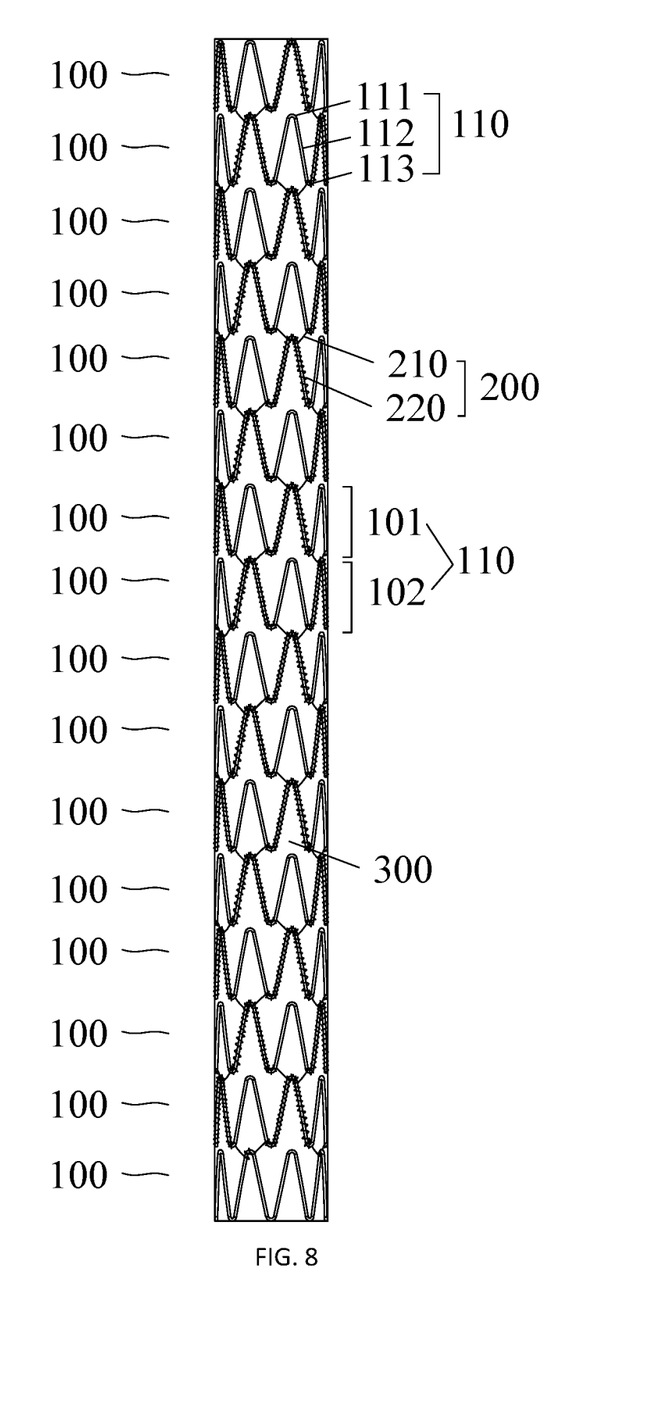
FIG. 8 is a schematic structural view of a stent according to fifth embodiment of the present disclosure.

This highly flexible stent includes, in addition to the bare stent formed by the annular supports 100, a further tubular membrane 300. The annular supports 100 are axially arranged in sequence and fixed on an inner surface or/and an outer surface of the membrane 300. In this embodiment, a two-layer membrane 300 is provided, including an inner membrane layer and an outer membrane layer, which is formed by mounting two tubular membrane together, with one tubular membrane surrounding the other. The annular supports are arranged between the inner membrane layer and the outer membrane layer.

As shown in FIG. 8, the inner membrane layer is a tubular one-piece structure, and is located in an inner layer of the stent for supporting the tubular structure of the whole stent. The outer membrane layer is a tubular one-piece structure located at the outermost layer of the stent, and covers the outer surfaces of the annular supports 100, the first flexible connecting members 210 and the second flexible connecting members 220. The annular supports 100, the first flexible connecting members 210 and the second flexible connecting members 220 are sandwiched between the inner membrane layer and the outer membrane layer, so that the overall structure of the stent can be maintained. In order to further improve the stability of the entire stent structure, the inner membrane layer and the outer membrane layer may be integrated together by thermal bonding. In this embodiment, the material of the membrane 300 is a high molecular membrane such as PET or ePTFE. The inner membrane layer and the outer membrane layer each may be formed by combining 1 to 5 layers of high molecular membranes, for example, by combining 3 layers of membrane structures. In case that the first flexible connecting members 210 and the second flexible connecting members 220 are made of PET wire, PP wire, PTFE wire, etc., after thermal pressing, the first flexible connecting members 210 and the second flexible connecting members 220 wound on the supports can be well fused with the polymer membrane, and the overall structure of the stent with membrane is more stable.

The structures of the annular supports 100, the first flexible connecting members 210 and the second flexible connecting members 220 are the same as those of the first embodiment, and will not be described here again.

Sixth Embodiment

This embodiment is a modification on the basis of the third embodiment.

Figure 9:
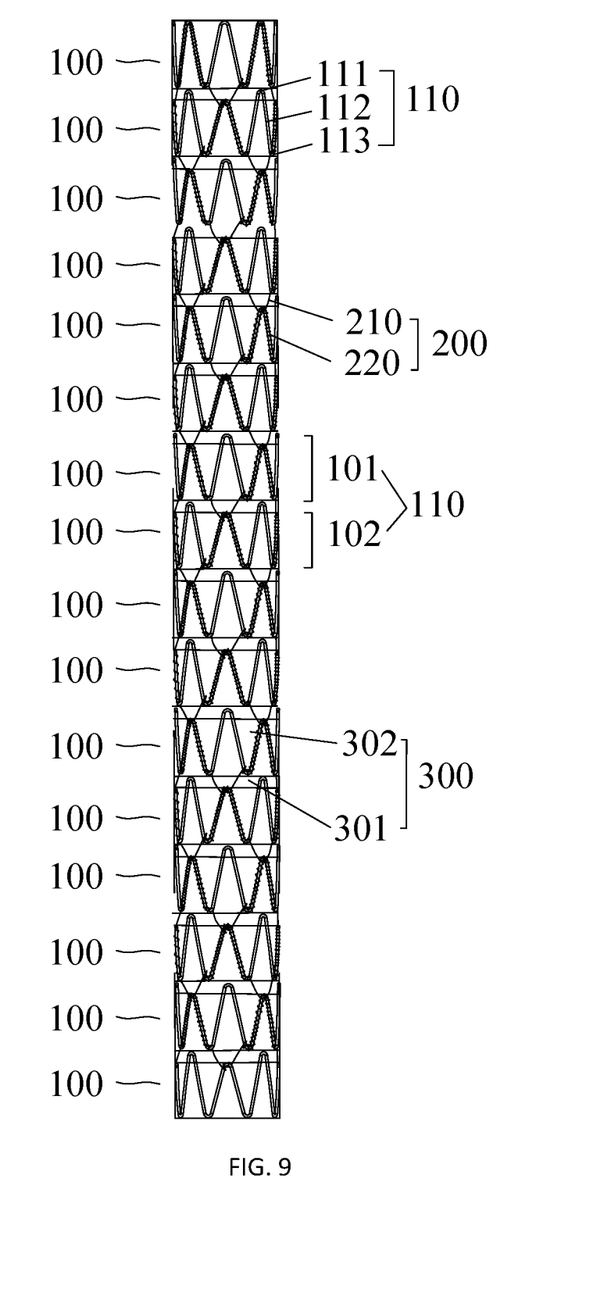
FIG. 9 is a schematic structural view of a stent according to sixth embodiment of the present disclosure.

As shown in FIG. 9, in this embodiment, a membrane 300 is provided inside and outside the bare stent of the third embodiment. Preferably, the annular supports 100, except for the first loop of annular support 100 at the proximal end, are unequal-height-wave supports each of which is formed by high-height-wave support units and low-height-wave support units. The unequal-height-wave supports are fixed on the inner surface or the outer surface of the membrane 300. The low-height-wave support units are fixed to the membrane 300, whilst the peaks 111 of the high-height-wave support units 110 are not fixed to the membrane 300.

Preferably, the stent includes the annular supports 100, the first flexible connecting members 210, the second flexible connecting members 220, an inner membrane layer 301 and an outer membrane layer 302. The annular supports 100, the first flexible connecting members 210 and the second flexible connecting members 220 are located in a middle layer of the stent, between the inner membrane layer 301 and the outer membrane layer 302. This embodiment differs from the fifth embodiment in that the structure of the bare stent includes an unequal-height-wave structure, and the peaks 111 of the high-height-wave support units are not covered by the outer membrane layer 302.

Figure 10:
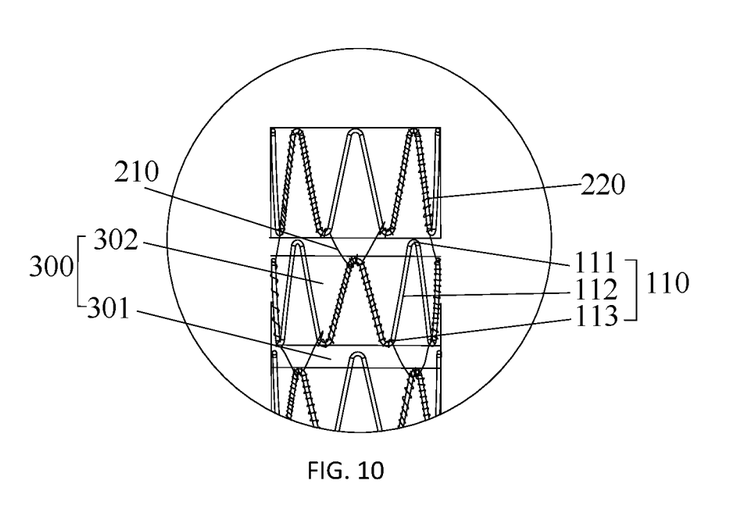
FIG. 10 is a partially enlarged view of the sixth embodiment of the present disclosure.

The inner membrane layer 301 is of a tubular one-piece structure, and is located inside the annular supports 100. As shown in FIG. 10, the outer membrane layer 302 is multi-segment annular structure with multiple annular segments arranged spaced apart in the axial direction. Each segment of the outer membrane layer 302 covers on the annular supports, from the peaks 111 of the low-height-wave support units of an annular support 100 to the valleys 113 of the same annular support 100, leaving the peaks 111 of the high-height-wave support units exposed. When the stent is bending, the unrestrained peaks 111 do not restrict the bending movement of the stent with membrane, such that by way of the membrane 300 in this embodiment, the axial compliance of the stent is improved.

Other structures are the same as those in the third embodiment, and will not be described here again.

What is claimed is:

1. A highly flexible stent comprising a plurality of annular supports arranged in an axial direction, each of the annular supports being formed by a plurality of wave-shaped support units connected end to end, each of the support units comprising a peak, a valley, and a bar connected between the peak and the valley,
wherein, within two adjacent annular supports, the peaks of the support units of one annular support are connected to the valleys of the support units of an other annular support by first flexible connecting members, and the first flexible connecting member further extends to and is wound onto at least one support unit to form a second flexible connecting member; and
wherein the second flexible connecting member at least wound around the support unit from the peak to the bar or from the valley to the bar, and some of the peaks are skipped and not restricted by the first flexible connecting members.

2. The highly flexible stent according to claim 1, wherein the support units in different annular supports have the same wavelengths, and the supports units are respectively aligned in the axial direction and arranged in columns, and wherein within two adjacent annular supports, the first flexible connecting member is connected between a peak and a valley which are located in different columns in the axial direction.

3. The highly flexible stent according to claim 2, wherein the first flexible connecting member is connected between the peak of one support unit and both the valleys of the support units of the adjacent annular support in two adjacent columns, to form a connection structure having a shape of an inverted, truncated V.

4. The highly flexible stent according to claim 3, wherein within one annular support, each valley is connected with the first flexible connecting member, and a portion of the peaks are connected to the first flexible connecting members.

5. The highly flexible stent according to claim 1, wherein the first flexible connecting member is continuously connected with at least the second flexible connecting member in a column adjacent to the support unit to which the first flexible connecting member is connected.

6. The highly flexible stent according to claim 5, wherein the first flexible connecting members connecting the support units of two axially adjacent annular supports are continuously connected to the second flexible connecting members on the support units of one of two axially adjacent annular supports.

7. The highly flexible stent according to claim 6, wherein the first flexible connecting members connecting the support units of two axially adjacent annular supports and the second flexible connecting members on the support unit of one of the two axially adjacent annular supports are formed as one-piece structure.

8. The highly flexible stent according to claim 7, wherein the first flexible connecting member and the second flexible connecting member of at least two adjacent columns in the axial direction are formed as one-piece structure from a proximal end to a distal end.

9. The highly flexible stent according to claim 1, wherein the second flexible connecting member is spirally wound on the support unit with several circles, and a space is defined between every adjacent circle of the second flexible connecting member.

10. The highly flexible stent according to claim 1, wherein the support units comprise wound support units with the second flexible connecting members wound there around, and bare support units without a second flexible connecting member wound there around, and wherein the wound support units and the bare support units are alternately arranged.

11. The highly flexible stent according to claim 10, wherein within a same annular support, the wound support units and the bare support units are alternately and repeatedly arranged.

12. The highly flexible stent according to claim 10, wherein in the axial direction, the wound support units and the bare support units of different annular supports are alternately and repeatedly arranged in a column.

13. The highly flexible stent according to claim 10, wherein the wound support unit is a full-wound support unit in which the peak, the bar and the valley are all wound by the second flexible connecting member.

14. The highly flexible stent according to claim 1, wherein the annular support is an unequal-height-wave support formed by high-height-wave support units and low-height-wave support units, and wherein the peaks of the low-height-wave support units are connected to the first flexible connecting members, and the peaks of the high-height-wave support units are not connected to the first flexible connecting members.

15. The highly flexible stent according to claim 1, wherein the first flexible connecting member are connected between the peak and the valley of support units in different annular supports by means of knotting or winding.

16. The highly flexible stent according to claim 1, wherein the stent further comprises a tubular membrane, and the annular supports are axially arranged and fixed on an inner surface or/and an outer surface of the membrane.

17. The highly flexible stent according to claim 16, wherein the annular support is an unequal-height-wave support formed by high-height-wave support units and low-height-wave support units, and the unequal-height-wave support is fixed on the outer surface or the inner surface of the membrane, and wherein the low-height-wave support units are fixed to the membrane, and the peaks of the high-height-wave support units are not fixed to the membrane.

18. The highly flexible stent according to claim 16, wherein the membrane comprises an inner membrane layer and an outer membrane layer, and the annular supports are arranged between the inner membrane layer and the outer membrane layer.

19. The highly flexible stent according to claim 1, wherein the first flexible connecting members are wound around and fixedly connected to adjacent annular supports at every other peak to establish diamond-shaped closed loops, delimited between the first flexible connecting members and the two adjacent annular supports, and diamond-shaped open loops formed by adjacent annular supports not connected with one another.

20. The highly flexible stent according to claim 19, wherein the diamond-shaped closed loops and the diamond-shaped open loops are alternately arranged, and some of the peaks of the diamond-shaped open loops are configured for movement.

* * * * *